(12) United States Patent
Briones Fernández-Pola

(10) Patent No.: US 8,592,753 B2
(45) Date of Patent: Nov. 26, 2013

(54) ION MOBILITY SPECTROMETER

(75) Inventor: Fernando Briones Fernández-Pola, Soto del Real (ES)

(73) Assignee: Ramem S.A., Madrid (ES)

( * ) Notice: Subject to any disclaimer, the term of this patent is extended or adjusted under 35 U.S.C. 154(b) by 206 days.

(21) Appl. No.: 13/321,250

(22) PCT Filed: May 18, 2009

(86) PCT No.: PCT/ES2009/070164
§ 371 (c)(1),
(2), (4) Date: Nov. 18, 2011

(87) PCT Pub. No.: WO2010/133714
PCT Pub. Date: Nov. 25, 2010

(65) Prior Publication Data
US 2012/0061563 A1    Mar. 15, 2012

(51) Int. Cl.
*H01J 49/40* (2006.01)
*C02F 1/34* (2006.01)

(52) U.S. Cl.
USPC ............ 250/282; 250/281; 210/748.02

(58) Field of Classification Search
USPC ......... 250/281–284, 287, 288, 290, 292, 293; 210/748.01, 748.02, 748.05
See application file for complete search history.

(56) References Cited

U.S. PATENT DOCUMENTS

| | | | | |
|---|---|---|---|---|
| 4,877,516 A * | 10/1989 | Schram | ............ | 209/155 |
| 5,190,667 A * | 3/1993 | Jaeger | ............ | 210/748.01 |
| 6,216,538 B1 | 4/2001 | Yasuda | | |
| 6,454,945 B1 * | 9/2002 | Weigl et al. | ............ | 210/634 |
| 6,749,733 B1 | 6/2004 | Sibbett | | |
| 8,272,576 B2 * | 9/2012 | Doak et al. | ............ | 239/8 |
| 2007/0044580 A1 | 3/2007 | Arcas et al. | | |

FOREIGN PATENT DOCUMENTS

| | | |
|---|---|---|
| EP | 1923699 | 5/2008 |
| WO | 2004077016 | 9/2004 |
| WO | 2006084363 | 8/2006 |

* cited by examiner

*Primary Examiner* — Bernard E Souw
(74) *Attorney, Agent, or Firm* — Dickinson Wright PLLC

(57) ABSTRACT

This invention refers to an ion mobility spectrometer in a fluid subjected to an electric field and an acoustic wave for the selective detection, classification and quantitative determination of the concentration of charged particles, based on their electrical mobility. The functioning of this device is based on the application of an electric field in a classification region occupied by a fluid. The electric field provokes drift of the charged particles through the classification region. The drifting particles suffer a lateral perturbation in their trajectory due to an oscillatory movement of the fluid in which they are immersed when this is subjected to an acoustic wave. Both the spectrometer and the method of discrimination and detection of the current of charged particles is the object of this invention.

17 Claims, 6 Drawing Sheets

ION MOBILITY SPECTROMETER

CROSS-REFERENCE TO RELATED APPLICATIONS

This application is a National Stage of International Application No. PCT/ES2009/070164, filed May 18, 2009. The entire disclosure of the above application is incorporated herein by reference.

DESCRIPTION

1. Object of the Invention

This invention relates to an ion mobility spectrometric device which permits classification of particles or ionised molecules using a relative displacement of its components or even acoustic modulation.

2. Background to the Invention

Various devices exist which permit classification of ionised particles depending on their electrical mobility. The most relevant devices, in terms of their high resolution and sensitivity, are DMAs (Differential Mobility Analyser) and the most relevant one in terms of its portability is the IMS (Ion Mobility Spectrometer).

The physics behind a DMA may be summarised in the following manner: ions, molecules or charged particles to be analysed are dragged through a region occupied by a fluid due to the presence of an electric field. These ions or charged particles are diverted through the displacement of fluid in a direction perpendicular to the electric field. The greater or lesser separation of their trajectory with respect to the electric field lines depends on the mobility of the particles.

In conventional DMA devices, the resolution grows according to the reduction in time of flight (TOF) as the dispersion due to Brownian diffusion (through thermal agitation) is less. This tendency makes electric fields and speeds involved increasingly greater in order to achieve better resolutions.

It soon becomes obvious that an increase in the flow rate requires greater efforts to keep the turbulence under control, as the Reynolds numbers involved are extremely critical. Besides this, there is the additional complication of increasingly greater Mach numbers and entry in supersonic regime.

This type of device is used in the detection of substances such as narcotics, chemical agents or explosives in public places. The need to establish a crossed flow imposes the use of ducts and pumps which significantly increase the size of the final device even when the classification region is small. This configuration implies large dimensions of the device that hinder and even prevent the application of DMAs in such scenarios.

Alternatives to DMAs in order to permit reduction of their size and complexity, often at the expense of their resolution and sensitivity, are those provided by Ion Mobility Spectrometers (IMS).

TOF spectrometers select ionised particles according to their time of flight, accelerated in a longitudinal uniform electric field travelling in a vacuum, from an initial instant defined by grids which act as switches for the charged particles.

The most common of the IMS are based on the application of a longitudinal direct current (DC) electric field and a superposed alternating current (AC) electric field perpendicular thereto. Only ionised particles which are not diverted and captured by AC polarised lateral electrodes can be detected by an output electrometer.

SUMMARY OF THE INVENTION

The present invention relies on a different and alternative principle of operation than the prior art: Particles drifting in a DC electric field are submitted to a lateral oscillatory displacement of their trajectory, preferably by the effect of an acoustic wave, and are preferably detected as a differential AC current collected on appropriate electrodes for instance by a phase sensitive AC amplifier (commonly known as lock-in) tuned to the acoustic wave frequency. The phase of this current relative to the reference signal of the lock-in will depend on the value of the DC electric field and the mobility of the ion species.

In a preferred embodiment of the invention, the proposed acoustic modulation of the drifting particles of the trajectory allows for an AC detection of the ion current and classifying the particles according to their mobility. Acoustic modulation substituting an AC electric field avoids capacitive coupling to the lock-in detector.

A first aspect of the invention is a device, an ion mobility spectrometer, for classifying ionised molecules or charged particles (which shall be referred to globally throughout this description as "charged particles") in accordance with their mobility while drifting in a fluid subjected simultaneously to a DC electric field and to an oscillating displacement in a direction transversal to the electric field. This device comprises a classification region defined by a volume containing a fluid, such that in the boundary of the surface of this classification region there is at least one injector in a first place from where the injection or introduction of the charged particles takes place, and at least a second place as destination of the charged particles. Both the first and second places are geometric places situated at the boundary of the volume of the named classification region. This classification region has its boundary surface preferably coinciding with the internal surface of the device which defines it, except for the possible presence of slits or surfaces through which the charged particles are either injected or introduced in the volume control or either removed therefrom.

The device also comprises a means for generating an electric field in the classification region which is able to drag along the charged particles from the first injection or introduction place towards the second place. This electric field is the one which, depending on the electrical mobility, drags the charged particle in a greater or lesser transit time between the two geometric places which is generally known as time of flight. The electric field value is therefore a variable of selection of mobilities of the charged particles of this device.

In a preferred embodiment of the invention, the classification region is limited, among other walls, by two facing parallel plates. The first geometric place is located in a plate where the charged particles are injected and the second geometric place is located in the other plate where the charged particles arrive, that is, the receptor. It is between these plates that the electric field which drags the charged particles from one plate to the other is established.

Additionally there are driving means that are able to provide a oscillating displacement acting onto the fluid with respect to the injector in the first place and the receptor in the second place, onto the injector in the first place with respect to the fluid and the receptor in the second place onto the receptor in the second place with respect the injector in the first place and the fluid, or simultaneously onto the injector in the first place and the receptor in the second place with respect to the fluid, wherein this displacement is in a direction essentially transversal to the direction of the electric field.

As an example of an embodiment, these means, according to the first case, may be loudspeakers arranged on both sides of the classification region and situated opposed to each other, or appropriate mechanical vibrators.

Optionally, it is also possible to incorporate electronic means for amplification and detection in phase with respect to the modulating acoustic wave, or "lock-in" detection, of the current of the charged particles.

In order to carry out this particular mode of embodiment, the plate where the second geometric place is situated is provided with electrodes. The electrodes are situated at either side of a geometric second place, in the rector, and enable the charged particles current to be collected in a differential mode by an AC amplifier.

In an example of an embodiment of the invention, the amplification of the current originated by the collected charged particles on the electrodes is carried out by means of a low noise differential AC amplifier.

This is an important feature which differentiates, among others, the invention with respect to conventional IMS. If the fluid does not suffer any disturbance, given their nil velocity, the charged particles would arrive at the place established by the electric field lines except for the Brownian diffusion, that is, what has been termed the second geometric place. An oscillating lateral displacement of the charged particles trajectory is generated for instance when the fluid is subject to an acoustic wave generated transversally and the charged particles may incide alternately on conducting electrodes arranged on either side of the second place.

In fact, in an embodiment of the invention, the first geometric place coincides with a slit for injecting charged particles and the second geometric place coincides with a second slit, parallel to the first one, for optional exit of non collected charged particles.

Similarly, according to another example of an embodiment, it is possible to make use of more than one pair of facing slits, for example, to increase the collected current.

The acoustic wave, in addition to establishing a lateral disturbance in the trajectory of the particles, generates pressures maxima and minima (nodes and anti-nodes) which may modulate the entering current of charged particles to the classification or drift space, acting as modulator of this current of charged particles, defining the moment of exit with respect to the moment of arrival and permitting its selection using the time of flight. The pressure increments in the entry slit block the entry of charged particles and the pressure drops facilitate their entry. If the slit were to be found in a node of the acoustic wave, modulation through this mechanism would not occur; and in particular nor would it produce the disturbance which permits discrimination in this invention.

In the event of wishing to intensify the amplitude of this modulation of the injection of charged particles, it is established that an adequate alternate voltage will be applied, coming from the voltage applied to the excitation means generating the acoustic wave and in a definite phase with respect to the reference signal for the lock-in detection system, to appropriate electrodes situated at the entry slits, in order to restrain the injection of charged particles during part of the modulation cycle.

Those charged particles which, for a specific value of the electric field, reach the exit slit in phase with the maximum transversal displacements of the acoustic wave, will deposit their charge in an alternate manner on the electrodes situated on both sides of the slit and therefore, will generate an alternative current which is amplified and detected by means of a (lock-in) detector tuned to be in phase with a reference taken from the voltage applied to the excitation means generating the acoustic wave. This current, detected and amplified, is the one which is considered in the cases indicated below.

The description of the invention is extended, along with the different modes of carrying it out, in the section concerned with the detailed explanation of the invention.

DESCRIPTION OF DRAWINGS

The present descriptive report is accompanied by a set of plans illustrating a preferred embodiment which are in no way restrictive of the invention.

DETAILED EXPLANATION OF THE INVENTION

Having established the basic functioning mode of the sensor device as well as some examples of an embodiment, it is necessary to detail the principle of operation as well as some additional of embodiments supported by the figures.

Figure 1:
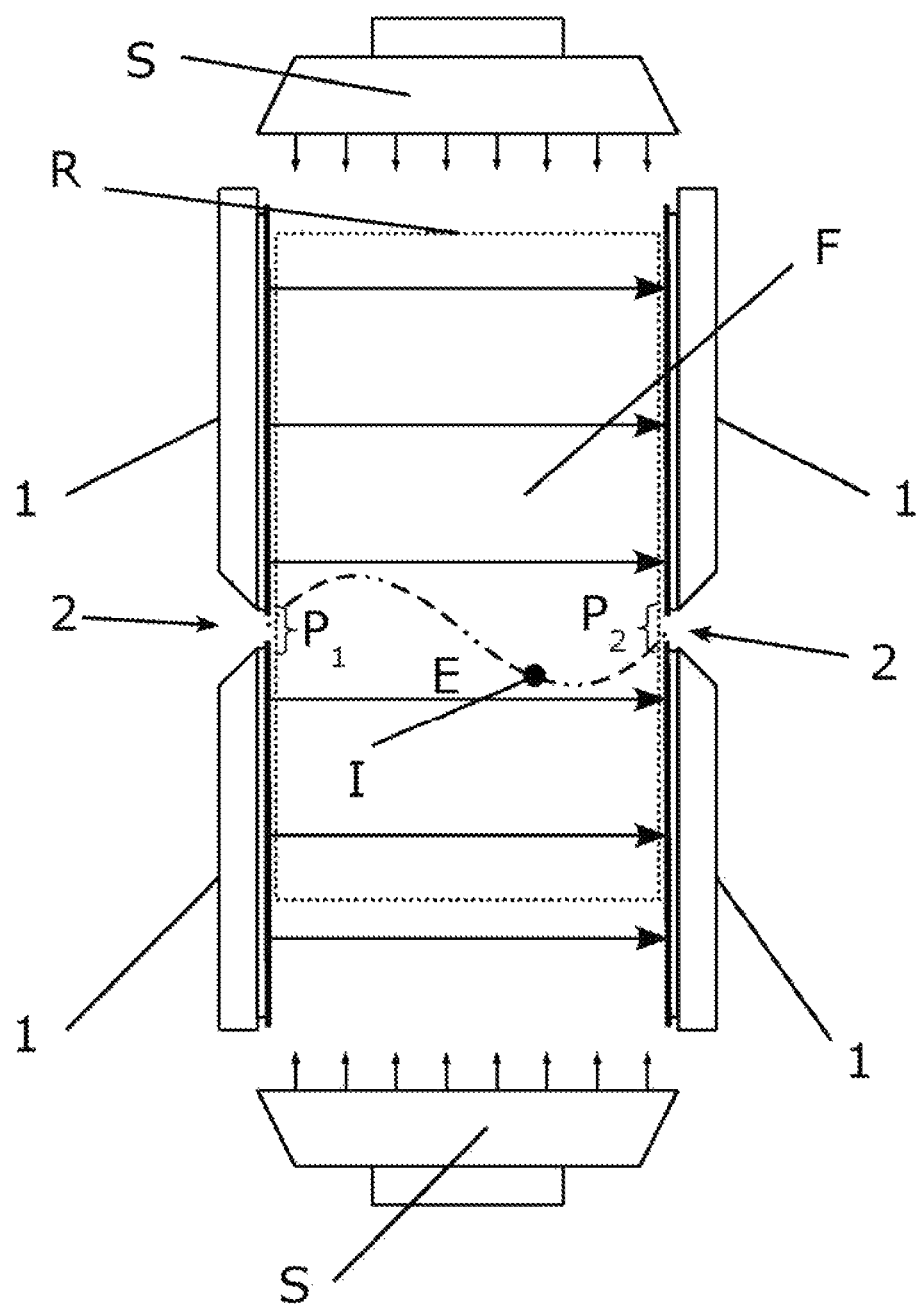
FIG. 1 shows a diagram of a specific mode of embodiment of the invention. This representation shows a side view of the device in order to view in diagrammatic form and without corresponding to the real dimensions, the trajectory of the charged particle. This same figure includes a detail of the second place where the charged particles arrive, showing the presence of collector electrodes, in addition to a slit.

FIG. 1 shows a first example of an embodiment representing a volume which establishes a region (R) of classification or analysis. The limits of this region for this example of an embodiment are two facing parallel plates.

Two geometric places are particularly relevant in these plates, known as first place ($P_1$) situated to the left and second place ($P_2$) situated on the right. At all times, left, right or any other position or orientation term is indicated interpreted on the basis of the orientation of the drawings of FIGS. 1 to 2. These positional and orientation terms should therefore be interpreted relative to the figures, without these descriptive terms employed implying any restriction on overall orientation of a real device which reproduces any mode of embodiment of the invention.

The first place ($P_1$) corresponds to the place of injection of the charged particles to be classified. In the examples of an embodiment, this geometric place corresponds mainly to a slit (2) through which the charged particles enter.

The second place ($P_2$) corresponds to the main arrival place of the charged particles. It is not essential to have a slit (2) in order for the invention to function but it is desirable to have an exit for renewal of the drift gas if it is needed. Similarly the use of a slit (2) is considered to be adequate when it is wished to couple a second measurement device which operates on the actual particle when it exits the device in this invention or, for example, a storage medium for subsequent treatment of the particle is used.

The particles injected from the first place ($P_1$) are carried or driven by the electric field (E) generated by the application of a potential to the lateral polarisable electrodes (1).

According to this example of an embodiment, in the absence of disturbances to the fluid field (F) the charged particle (I) will move horizontally along a straight to the second place ($P_2$).

In this example of an embodiment, the presence of an acoustic source (5) introduces oscillations of the fluid field (F) through propagation of the acoustic pressure waves in a direction transversal to the electric field (E). These waves will disturb the trajectory of the charged particles (I) which travel through the fluid.

When the transversal dimensions of the device are comparable or multiple of the wavelength of the acoustic wave, and a resonating acoustic cavity is therefore configured for a specific excitation frequency, the entry and exit slits (2) should coincide preferably with the anti-nodes or positions of maximum amplitude of oscillation in order to optimise the effect of the transversal oscillation through pressure variation.

Its relative position will be defined in such a way that the oscillation phases coincide with all the slits (2), so that they may add in phase the ion currents or currents of charged particles captured by their lateral polarisable electrodes (1).

For low frequencies or wavelengths much bigger than the dimensions of the device, on the contrary, the amplitude of the oscillation will be independent on the position and multiple pairs of slits may be arranged in parallel and at any distance between each other, without any restriction other than that which determines the width of the diffusion cone of the particles for each time of flight.

A more extensive explanation of the diffusion cone will be provided below.

The theoretical calculations carried out in order to generate a behaviour model of the device allows to observe that the trajectories of the charged particles are oscillating, sinusoidal in first approximation.

The wavelength L of the oscillation is $L = Z \cdot E / f$ where Z is the electrical mobility normally measured in $m^2/Vs$, E is the electric field (V/m) and f the frequency (1/s) of the disturbance.

For each frequency f, and separation dimensions of the first and second places corresponding to the entry and arrival of the charged particles (I), and value of the electrical mobility Z, the value of the electric field (E) is one of the most important variables for establishing a focus of the trajectories of the charged particles (I) towards the second place ($P_2$).

Without taking into account Brownian diffusion, all the trajectories of the particles with the electrical mobility Z for which the focus has been defined will arrive at the second place ($P_2$). In the preferred embodiment, that place of arrival of the second place ($P_2$) is an exit slit (2).

The second place ($P_2$) is a geometric place of arrival of the charged particles (I), whether they are focused or not; and it may be greater than the first place ($P_1$) due to the increased width due to the lack of focus.

The remaining particles, those which do not verify the focusing condition, arrive out of focus impacting on one side or the other, above or below the slit (2) and always considering the relative position shown in the figures, according to whether the electrical mobility Z of the ion (I) is greater or less, and therefore its wave length L is different from the distance between the first ($P_1$) and second ($P_2$) places.

In the example of a preferred embodiment electrodes (4) are used, situated above and below the slits (2). These electrodes (4) are deposited on the surface of the plates and are insulated from them (1) using a dielectric (3).

Graph 5 shows the results of a numerical simulation of the trajectories of charged particles (I) with different electrical mobility Z. The overimposition of the very close lines does not allow a clear view of the various trajectories followed, thus a dotted circumference is situated at the right of the graph, in the arrival zone of the trajectory lines, and therefore this area has been amplified in FIG. 6.

Figure 6:
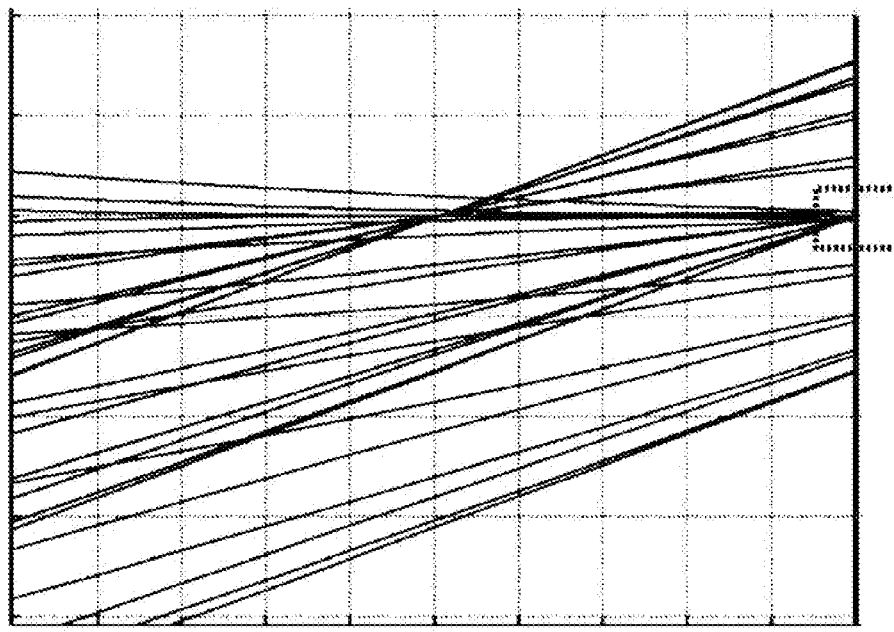

FIG. 6 also shows the trajectories in the zone of arrival, highlighting only those focalized in the collection point [that which will correspond to the slit (2)] using a dotted rectangle.

In an example of an embodiment for a 4 kHz frequency, a 5 mm electrode distance and a typical mobility of $1e-4\,m^2/Vs$; if we intend the wavelength to be L=5 mm a voltage of 1 kV is required, where the time of flight will be 0.25 ms.

Figure 7:
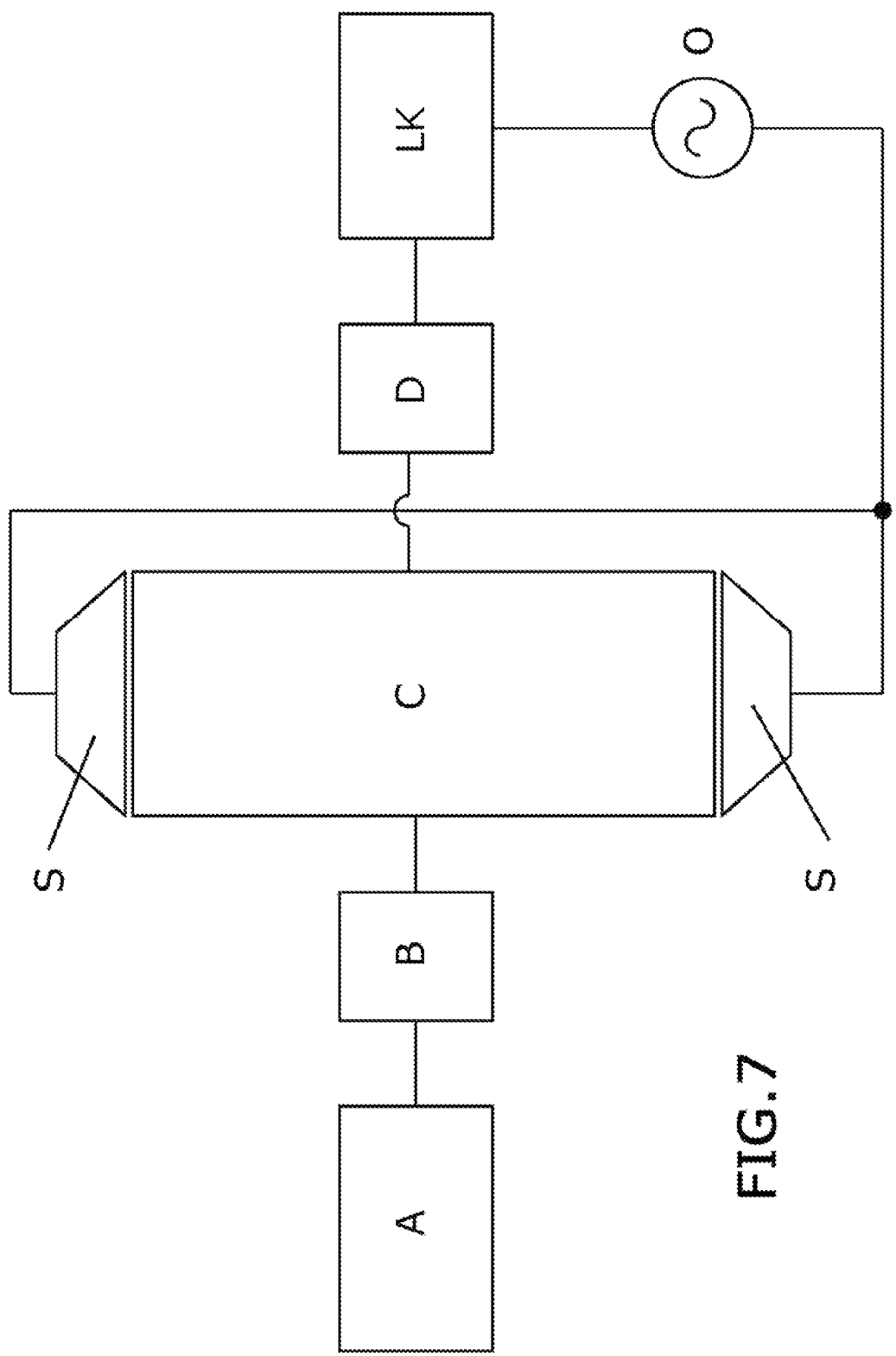
FIG. 7 shows a general diagram of an installation in which one of the components is the ionic mobility spectrometer according to any of the previous examples.

FIG. 7 shows a general diagram of the operation of a spectrometer (C) such as the one in this invention. This spectrometer is fed with charged particles generated by a charger (A) which delivers the charged particles to a modulator (B).

The modulator (B) controls whether or not the charged particles (C) enter the spectrometer (C) and it is represented independently of the control of injection of charged particles is made taking into account the regulation of the pressure changes when the slit (2) coincides with the pressure anti-nodes of the acoustic wave.

At the ends of the spectrometer (C) the fluid (F) acoustic excitation means inside the spectrometer (C) are shown as trapezia.

These means are excited by an oscillator (O) which also provides a reference signal for the lock-in device (LK) using a reference signal.

In turn, the lock-in (LK) device (phase detection) receives the signal from a differential amplifier (D) which amplifies the differential AC current collected by the electrodes (4.1, 4.2) situated above and below the second places ($P_2$) or the slits (2) if these are present.

As it has been indicated, in order to increase the resolution and signal to noise ration of the sensor, in this example of an embodiment, lock-in (LK) techniques or detection in phase are used. This method of synchronous detection in phase consists of amplifying only the alternate component of the current which has the same frequency as the oscillatory displacement or the acoustic modulation f and provides a reference in order to obtain its amplitude at a well defined phase with respect to the reference signal.

Figure 4:
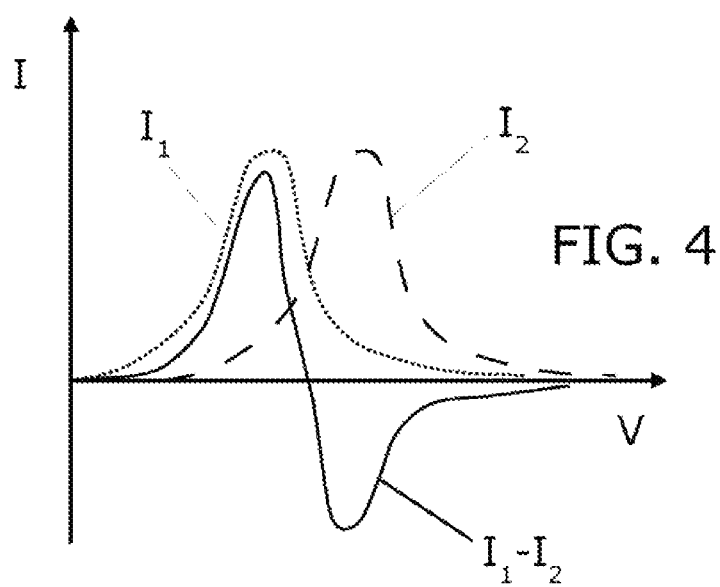
FIG. 4 is a graph showing the intensity of the electric current collected by the upper and lower collector electrodes in an example of an execution in which the phase amplification is carried out. This graph shows superimposed the lock-in amplifier output signal crossing through zero every time charged particles with distinctive mobility arrives in phase to the collector electrodes.
Figure 5:
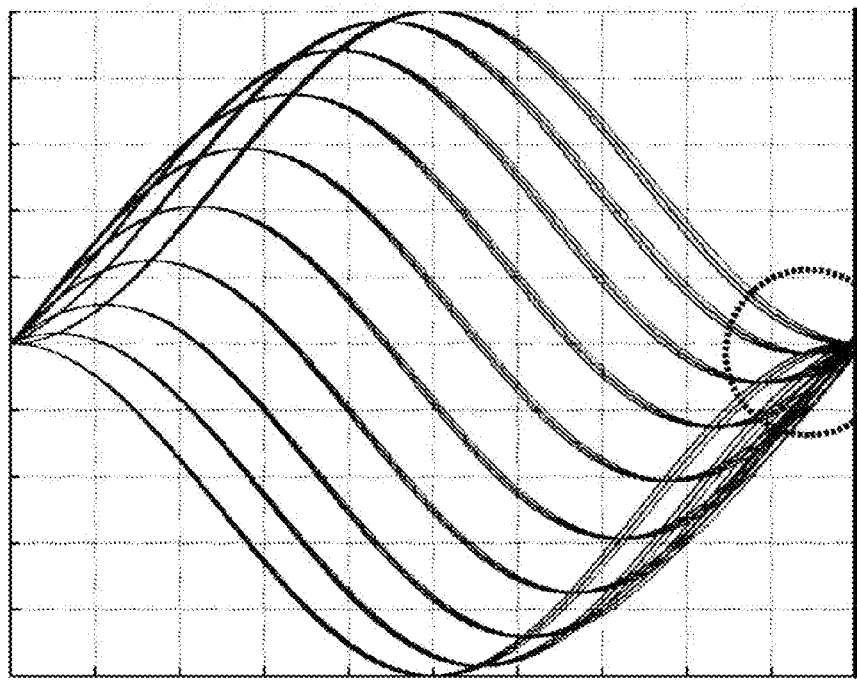
FIG. 5 is a graph obtained by means of numerical simulation for calculating trajectories generated by a specific f frequency of oscillation for charged particles with a different electrical mobility. The trajectories are seen with the same orientation as the diagram indicated in FIGS. 1 and 2. This graph shows in the area of arrival of charged particles, a dotted circumference indicating the amplification shown in FIG. 6. This FIG. 6 also shows a dotted rectangle indicating the area where the particles arrive on an exit slit.

As shown in FIG. 4, two ion currents are collected: a current ($I_1$) on the upper electrode (4.1) and a current ($I_2$) on the lower electrode (4.2). In this example of an embodiment the upper electrode (4.1) is situated above the slit (2) and the lower electrode (4.2) is situated below the slit (2).

The difference ($I_1$-$I_2$) is preamplified and detected by the lock-in amplifier which output changes sign and therefore crosses through a zero for each value of the polarization potential scan where the mobility of a particular ionized species results in a collection of such ions at the collecting electrodes (4) in phase with the reference signal. These zero crossing points determine the spectral positions of the various ions present in the sample gas. The difference between the maximum amplitude of the positive and negative peaks will be proportional to the concentration of the various ionized species to be analyzed.

In this particular embodiment, the applied potential between the polarisable electrodes (1) is the parameter that is varied through a spectral scan given that it is the one which offers greater facility of adjustment as the device geometry is already given and therefore the distance between the first place ($P_1$) and second place ($P_2$). Secondarily the frequency of the acoustic oscillation f may also be adjusted.

Figure 2:
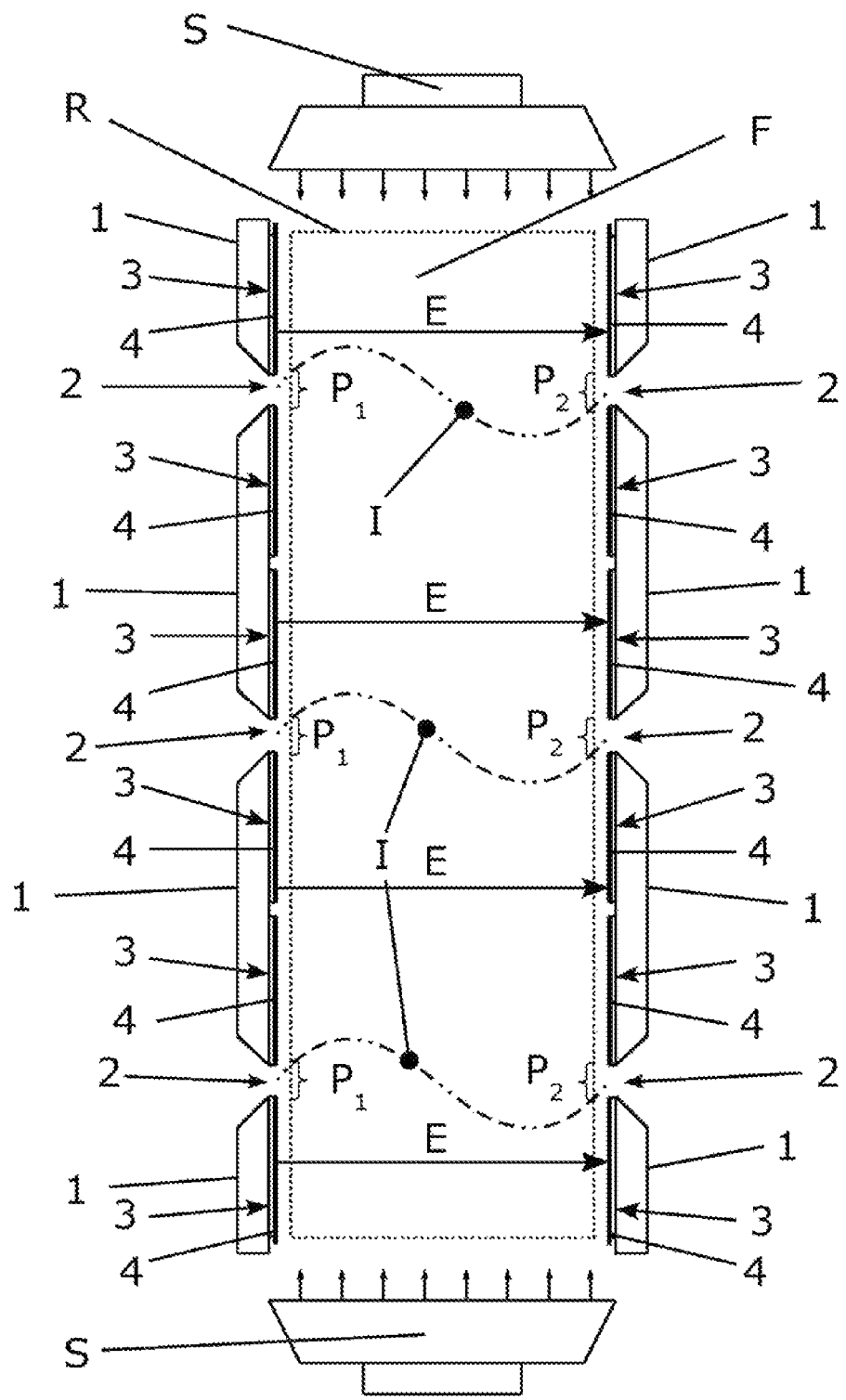
FIG. 2 shows a diagram of another example of an embodiment showing a configuration of multiple entries and exits sharing a single classification region.
Figure 3:
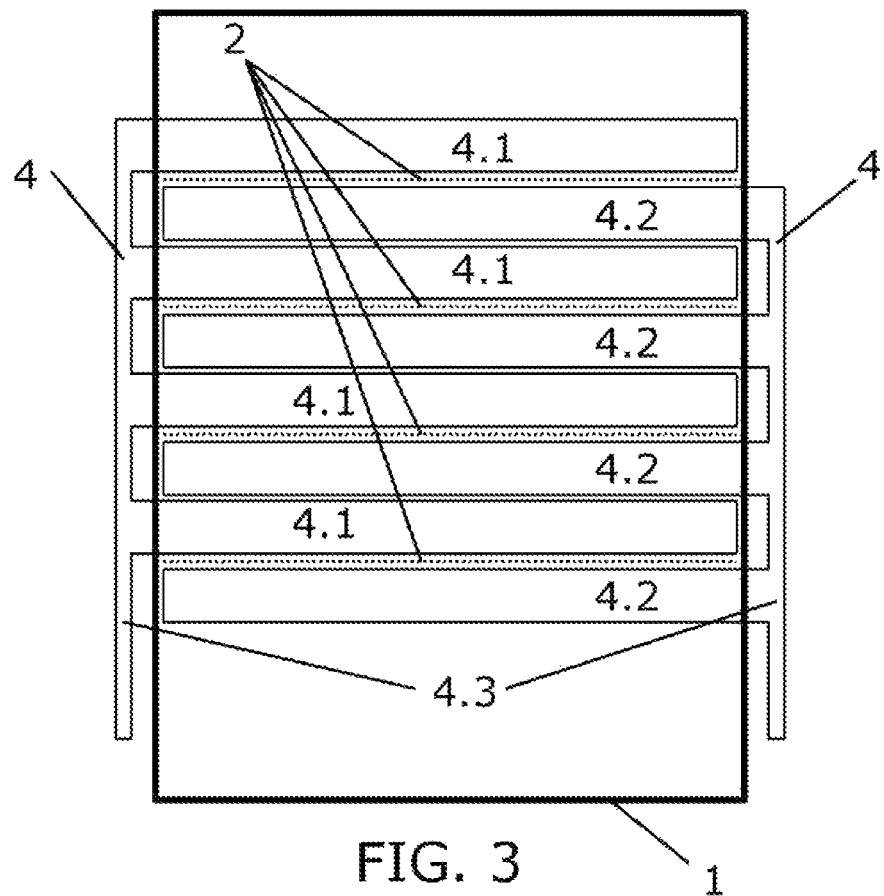
FIG. 3 shows a diagram of the surface of a sensor with multiple entries and exits where the charged particles arrive such as that in the example shown in FIG. 2. This representation highlights the arrangement of the collector electrodes and their extensions around each slit.

One example of embodiment of the invention incorporates more than one first place ($P_1$) and second place ($P_2$) as shown in FIG. 2. In this configuration there are multiple points of injection and arrival of charged particles arranged in parallel pairs along the length of the injection and the collection plates.

In the preferred example, slits (2) both in first places ($P_1$) and in second places ($P_2$) are also used. In this example of an embodiment, the detection of charged particles (I) arriving above and below the slit (2) is carried out on the upper extensions (4.1) and on the lower extensions (4.2) of the collector electrodes (4). All the upper extensions (4.1) are connected by a common connection rail (4.3). The same occurs with the lower extensions (4.2).

The resulting form of these collector electrodes (4) in this example of an embodiment has the shape of a double interdigited rake; that is, the extensions (4.1) of the first rake are situated in the upper part of each second place ($P_2$) and the extensions (4.2) of the second rake are situated on the lower part of each second place ($P_2$). In the preferred example they remain above and below the slits (2).

The advantage of this configuration is the possibility of increasing the sensitivity of the device without losing resolution, proportionally to the number of slits pairs, without any need to correspondingly multiply the number of amplifiers and lock-in detectors (LK), as it is possible to collect the ion currents in parallel by the interdigitated electrode rakes and to amplify a single differential current which is the sum of all the currents collected with identical phase.

In this configuration the oscillating impulsion means (S) are also shared. It is considered adequate that the oscillating impulsion means (S) are arranged in opposition, leaving between them the classification region (R).

In an example of an embodiment, the plate where the slit is situated (2) for entry or injection of the charged particles, is metallised and polarised with respect to the plate opposite the standard potential, variable during adjustment of the electrical drift field (E), in the range of 1-5 kV. However, in a specific embodiment of this invention, it will also be possible to establish a small transversal potential, dV, superimposed on the drift potential (E) in order to optimise the alignment of the ion trajectories with respect to the position of the exit slits.

In another specific embodiment it is also possible to use a second entry slit (2) above the first slit (2) and with a variable polarisation with respect to the first, in order to permit deviation and switching at will of the flow of charged particles, functioning as a synchronised injection window. This time window may be synchronised with the exciting means of the oscillating plates or acoustic modulation and by reducing its width, improve, in specific applications in which the densities of charged particles were sufficiently high, the spectral resolution at the expense of the sensitivity of the device.

The pressure variations in the space between plates corresponding to the acoustic wave, irrespective of whether or not it is stationary, may also provide for a modulation of the injection of charged particles through the entry slit (2) since the diffusion of charged particles across the slit (2) is hindered or promoted at any time by the variable pressure difference between the external medium and the interior medium situated between the electrodes (1, 4).

Figure 8:
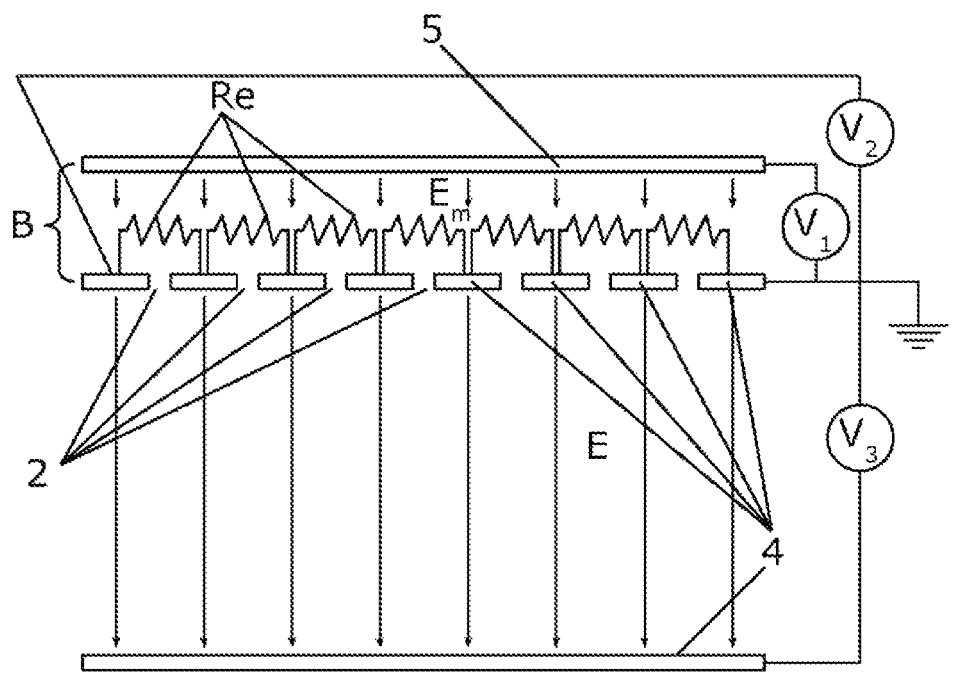
FIG. 8 shows a diagram of an example of an embodiment showing a mode of modulation of the injection of charged particles as well as an example of adjustment or correction of the parallelism of the electric field. This diagram is descriptive and the scales are not real.

FIG. 8 shows the modulator (B) according to an example of the invention. The presence of static charges in the lateral walls (not shown) or any other type of perturbation, may give rise to a lack of parallelism of the electric field (E) in the region (R) of classification. FIG. 8 shows a modulator (B) as well as the means which allow for the correction of deviations of the lines of electric field (E).

The modulator (B) in this example of an embodiment is situated in a space between a conducting grid (5) and the conductor (4) arranged at the entrance of the injection, for generation of the drift field (E) in the region (R) of classification.

Between both conductors (4, 5) a potential polarisation $V_1$ of is applied which generates an electric field ($E_m$) of modulation. The charged particles present in the space between both conductors (4, 5) are carried by the electric field $E_m$. If the electric field $E_m$ is oriented towards the interior of the classification region (R), the charges will be injected through the entry slits (2). The absence of polarisation or a polarization opposite to the previous one will give rise to no injection. This modulation may be synchronised with the pressure variations due to the acoustic wave in such a way that windows for opening are generated in coincidence with the pressure anti-nodes of the acoustic wave.

As described in the figure, the $V_1$ potential is applied between a conducting grid (5) and the conductor (4) arranged at the entry of the injection slits in order to generate the electric field (E) in the region (R) of classification.

At the same time, the second conductor (4) has been represented as comprising various elements which are connected to each other by a resistance (Re). This configuration gives rise to a voltage divider which, being polarised with a potential $V_2$ creates an oblique electric field (E) in the classification region (R). The potential $V_3$ establishes the intensity of the electric field (E) in the classification region (R) and the potential V2 permits adjustment of the parallelism of the same electric field (E).

It is also possible, instead of using a voltage divider, to use a resistive material polarised between its ends, so it generates a continuous potential gradient which also permits the correction of orientation of the electric field (E).

The injection of the charged particles may be facilitated by a slow continuous flow of the sample fluid through the slits (2).

The invention claimed is:
1. Ion mobility spectrometer which comprises:
   a classification region defined by a volume containing a fluid, such that in the boundary of the surface of this classification region there is at least one injector in a first place from where the injection or introduction of charged particles takes place, and at least a receptor in a second place as destination of the charged particles, means for generating an electric field in the classification region which is able to drag along the charged particles from the first injection or introduction place towards the second place, wherein there are driving means that are able to provide a relative oscillating displacement of the trajectory of the particles acting:

onto the fluid with respect to the injector in the first place and the receptor in the second place, or, onto the injector in the first place with respect to the fluid and the receptor in the second place, or onto the receptor in the second place with respect to the injector in the first place and the fluid, or simultaneously onto the injector in the first place and the receptor in the second place with respect to the fluid; and wherein this displacement is in a direction essentially transversal to the direction of the electric field.

2. The spectrometer according to claim 1 wherein there is no relative movement between the injector in the first place and the receptor in the second place and the oscillating displacement is that of the fluid relative to both, the injector in the first place and the receptor in the second place.

3. The spectrometer according to claim 1 wherein the classification region is at least limited by two parallel plates facing each other where on one of the plates is situated the first place and where on the other plate the second place is situated also facing each other in such a way that the relative oscillating movement is along a direction parallel to the plates.

4. The spectrometer according to claim 1 wherein the oscillating fluid driving means are means for generating acoustic waves operating at a predetermined f frequency.

5. The spectrometer according to claim 1 wherein the means for generating acoustic waves are dual and are situated in opposition in such a way that the region of classification is arranged between them.

6. The spectrometer according to claim 1 wherein the injector in the first injection place is provided with a slit for entry of the charged particles.

7. The spectrometer according to claim 1 wherein the means of generation of the electric field are polarisable electrodes arranged on both facing plates.

8. The spectrometer according to claim 7 wherein the polarisable electrodes are situated on the surface of the plates separated from said plates by a dielectric.

9. The spectrometer according to claim 3 wherein the electrode situated on the plate corresponding to the second place is in turn divided into two parts, one part being situated on one side of the second place and the other part situated on the other side of the second place taking one or the other side in the direction of the oscillatory displacement.

10. The spectrometer according to claim 3 where in the first plate there is a plurality of first places facing one by one a plurality of second places situated in the second plate operating with a classification region with a common fluid and means of providing an oscillating displacement of said fluid or of one or both plates which are also common.

11. The spectrometer according to claim 9 wherein the collector electrodes are provided with two sets of extensions distributed on one or the other side of the second places in the form of interdigited rakes where these are situated in such a way that: the extensions of one of the rakes are arranged on one side of the second places; and, the extensions of the other rake are arranged on the other side of the second places.

12. The spectrometer according to claim 9 wherein it is provided with a differential lock-in amplifier for detecting the alternated charged particles current consequence of the collected charged particles in the electrodes situated at one side and on the other side of the second places for the detection in phase with respect to the voltage applied to the means generating the oscillating displacement.

13. The spectrometer according to claim 1, wherein the injection of charged particles in the region of classification is modulated with a modulator having appropriate electrodes situated at the entry slit, in order to restrain the injection of charged particles or in order to modify the electric field distribution.

14. A method for the classification of charged particles according to their mobility in a fluid characterized by the fact that it makes use of a classification region defined by means of a volume in which there is said fluid, wherein:

the charged particles are injected through a first place ($P_1$) located on the boundary surface of the classification region, an electric field is provided to drag the charged particles injected at the first place to electrodes located at the sides of a second place ($P_2$) also located on the boundary surface of the classification region, an relative oscillatory displacement in a direction essentially transversal to the direction of the electric field is provided between the fluid and any of the first or second places or simultaneously both places, the arriving charged particles to the electrodes located at the sides of the second place ($P_2$) originate a differential AC current which is pre-amplified and detected in phase by a lock-in amplifier.

15. The method according to claim 14 wherein the potential which determines the electric field (E), the frequency of the relative oscillatory displacement or both are varied in order to obtain the spectral distribution of charged particles mobilites.

16. The method according to claim 14 wherein it incorporates an electric drift field transversal to the main electrical carrying field in order to optimize alignment of the ionic trajectories with respect to the position of the second place of arrival.

17. The method according to claim 14 wherein it incorporate means to restrain the injection of charged particles coupled to the excitations means generating the oscillatory displacement in order to restrain the injection of charged particles during part of the modulation cycle.

* * * * *